US012564566B2

(12) United States Patent
Pipingas et al.

(10) Patent No.: US 12,564,566 B2
(45) Date of Patent: Mar. 3, 2026

(54) USES OF LONG-CHAIN POLYUNSATURATED FATTY ACIDS

(71) Applicant: Swinburne University of Technology, Hawthorn (AU)

(72) Inventors: Andrew Pipingas, Mount Waverley (AU); Andrew Scholey, Clifton Hill (AU)

(73) Assignee: Swinburne University of Technology, Hawthorn (AU)

( * ) Notice: Subject to any disclaimer, the term of this patent is extended or adjusted under 35 U.S.C. 154(b) by 970 days.

(21) Appl. No.: 17/633,340

(22) PCT Filed: Aug. 7, 2020

(86) PCT No.: PCT/AU2020/050822
§ 371 (c)(1),
(2) Date: Feb. 7, 2022

(87) PCT Pub. No.: WO2021/022340
PCT Pub. Date: Feb. 11, 2021

(65) Prior Publication Data
US 2022/0280465 A1 Sep. 8, 2022

(30) Foreign Application Priority Data
Aug. 8, 2019 (AU) ................................. 2019902840

(51) Int. Cl.
| | |
|---|---|
| *A61K 31/202* | (2006.01) |
| *A61K 9/00* | (2006.01) |
| *A61K 35/60* | (2006.01) |
| *A61P 9/02* | (2006.01) |
| *A61P 9/12* | (2006.01) |
| *A61P 25/28* | (2006.01) |

(52) U.S. Cl.
CPC .......... *A61K 31/202* (2013.01); *A61K 9/0053* (2013.01); *A61K 9/0095* (2013.01); *A61K 35/60* (2013.01); *A61P 9/02* (2018.01); *A61P 9/12* (2018.01); *A61P 25/28* (2018.01)

(58) Field of Classification Search
CPC ..................................................... A61K 31/202
See application file for complete search history.

(56) References Cited

U.S. PATENT DOCUMENTS

2018/0044278 A1* 2/2018 Bazan ..................... A61P 25/28

FOREIGN PATENT DOCUMENTS

| | | |
|---|---|---|
| EP | 1800675 B1 | 5/2011 |
| RU | 2014141406 A | 5/2016 |
| WO | 2010088700 A1 | 8/2010 |

OTHER PUBLICATIONS

Elsen et al. Current Pharmaceutical Design, 2012, 18(16): 2375-2392.*
Mcmanus, S , et al., "Differential effects of EPA versus DHA on postprandial vascular function and the plasma oxylipin profile in men", J. Lipid Res 57, 1720-1727 (2016).
Chino, D , et al., "Acute Effects of Intravenous Administration of Polyunsaturated Fatty Acids on Blood Pressure and Heart Rate in U46619- and Noradrenaline-infused Rats", British Journal of Pharmaceutical Research 15(3), 1-12 (2017).
Mcnamara, R , et al., "Cognitive Response to Fish Oil, Blueberry, and Combined Supplementation in Older Adults with Subjective Cognitive Impairment", Neurobiol Aging 64, 147-156 (2018).
Morgese, M , et al., "Chlorella sorokiniana Extract Improves Short-Term Memory in Rats", Molecules 21, 1311, doi:10.3390/molecules21101311, 1-17 (2016).
Nilsson, A , et al., "Effects of supplementation with n-3 polyunsaturated fatty acids on cognitive performance and cardiometabolic risk markers in healthy 51 to 72 years old subjects: a randomized controlled cross-over study", Nutrition Journal 11 (99), 1-9 (2012).
Pase, M , et al., "The Effects of Long-Chain Omega-3 Fish Oils and Multivitamins on Cognitive and Cardiovascular Function: A Randomized, Controlled Clinical Trial", Journal of the American College of Nutrition 34 (1), 21-31 (2015).
Patent Cooperation Treaty , International Search Report and Written Opinion for PCT/AU2020/050822, 14 pages, dated Oct. 6, 2020.
Rontoyanni, V , et al., "A comparison of the changes in cardiac output and systemic vascular resistance during exercise following high-fat meals containing DHA or EPA", British Journal of Nutrition 108, 492-499 (2012).
Witte, A , et al., "Long-Chain Omega-3 Fatty Acids Improve Brain Function and Structure in Older Adults", Cerebral Cortex 24, 3059-3068 (2014).
Chinese Office Action, for CN Application No. 202080068283.7, 6 pages, dated Dec. 16, 2024. [including English Translation].
Li Guangzhi, "Coronary Heart Disease", China Pharmaceutical Science and Technology Press, p. 41 (2009).
Wang Hongxin, et al., "New Food Resource", China Light Industry Press, p. 273 (2002).

* cited by examiner

*Primary Examiner* — Rei Tsang Shiao
(74) *Attorney, Agent, or Firm* — Viksnins Harris Padys Malen LLP

(57) ABSTRACT

The present invention is directed to methods of acutely improving or enhancing cardiovascular and/or cognitive function, comprising the administration of LCPUFAs, in particular docosahexanoic acid (DHA), uses and compositions thereof.

11 Claims, 4 Drawing Sheets

USES OF LONG-CHAIN POLYUNSATURATED FATTY ACIDS

CROSS-REFERENCE TO RELATED APPLICATION(S)

This application claims priority to Australian Patent Application No. 2019902840 filed on Aug. 8, 2019.

TECHNICAL FIELD

The present invention broadly relates to methods for acutely improving/enhancing cardiovascular function and/or cognitive function in a human subject comprising administration of one or more long-chain polyunsaturated fatty acids.

BACKGROUND OF THE INVENTION

Long-chain polyunsaturated fatty acids (LCPUFAs) are an important nutritional component of the human diet, in particular omega-3 fatty acids such as eicosapentaenoic acid (EPA) and docosahexaenoic acid (DHA). Long-chain omega-3 fatty acids are generally sourced from seafood and dietary supplements. It is known that long chain omega-3 fatty acids are associated with a variety of health benefits, including lowering of triglyceride levels, improving vascular integrity, and improving cognitive function. A large number of studies have found that omega-3 fatty acids play an influential role in heart, brain and eye health. For example, a recent study suggests that EPA and DHA may have the ability to decrease heart rate and oxygen consumption during exercise, therefore contributing to enhanced physical and mental performance in athletes (People et al., *Journal of Cardiovascular Pharmacology*, 2008, 52: 540-547). Because of their essential nutritional role, compositions comprising omega-3 fatty acids are important in terms of both nutritional supplementation, and as pharmaceutical agents.

The health benefits of omega-3 fatty acids established to date are generally associated with chronic supplementation, for example in the form of fish oil, and nearly all human studies to date have focussed on longer term dietary aspects of long chain omega-3 fatty acids, supplementing study participants over weeks to years. Such studies are consistent with known physiological mechanisms of the gradual uptake of long chain omega-3 fatty acids into human tissue that is commonly measured by assessment of levels contained in erythrocyte membranes.

SUMMARY OF THE INVENTION

The present disclosure is predicated on the inventors' unexpected discovery that acute beneficial effects can be realised following LCPUFA administration.

According to a first aspect, the present disclosure provides a method for acutely improving/enhancing cardiovascular function and/or cognitive performance in a subject, the method comprising administering to the subject one or more long-chain polyunsaturated fatty acids (LCPUFAs).

In particular embodiments, the LCPUFAs are omega-3 fatty acids, such as DHA and/or EPA. The LCPUFAs may be present, for example, in triglyceride form, in phospholipid form, in ethyl ester form or in free fatty acid form. In particular embodiments as disclosed herein the LCPUFAs are present in triglyceride form.

The LCPUFAs may be present in one or more LCPUFA-containing oils. The LCPUFA-containing oil(s) may be naturally occurring or naturally derived, or may be synthetic. The LCPUFA-containing oil(s) may be rich in LCPUFAs. The LCPUFA-containing oil may be an oil obtained from a single cell organism, a plant oil or a fish oil, or a concentrated form thereof. In an exemplary embodiment the oil is a fish oil, such as tuna oil.

In some embodiments, the LCPUFAs may be microencapsulated. For example, the LCPUFAs may be microencapsulated in an encapsulant comprising one or more low molecular weight proteins. In some embodiments, such microencapsulation advantageously improves the oxidative stability of the LCPUFAs.

In some embodiments, the LCPUFAs are administered in a dose of at least about 500 mg, for example in a dose of about 4 g.

In some embodiments, improvement/enhancement of cognitive performance and/or cardiovascular function in a subject occurs within about 4 hours of administration of the LCPUFAs.

In some embodiments, the LCPUFAs are administered orally. In some embodiments, the LCPUFAs are added to a food or drink for consumption by the subject prior to administration.

In some embodiments, the improvement/enhancement of cognitive performance includes an improvement/enhancement in memory. The improvement/enhancement in memory may comprise an improvement/enhancement in stroop effect response time, incongruent stroop response time, contextual memory and/or spatial working memory. The subject may be, for example, mentally stressed, mentally fatigued and/or cognitively challenged.

In some embodiments, the improvement/enhancement of cardiovascular function includes a reduction in blood pressure and/or pulse pressure. A reduction in blood pressure may comprise a reduction in brachial and/or aortic systolic blood pressure, a reduction in brachial and/or aortic diastolic blood pressure, and/or a reduction in brachial and/or aortic mean arterial blood pressure. The subject may have, be predisposed to, or be at risk of developing high blood pressure. Typically a reduction in pulse pressure comprises a reduction in brachial and/or aortic pulse pressure.

According to a second aspect, the present disclosure provides use of one or more LCPUFAs in the manufacture of a medicament for acutely improving/enhancing cardiovascular function and/or cognitive performance in a subject.

According to a third aspect, the present disclosure provides one or more LCPUFAs for use in a method of acutely improving/enhancing cardiovascular function and/or cognitive performance in a subject.

following administration of Treatment 1 (placebo) or Treatment 2 (DHA-containing dose).

Figure 4:
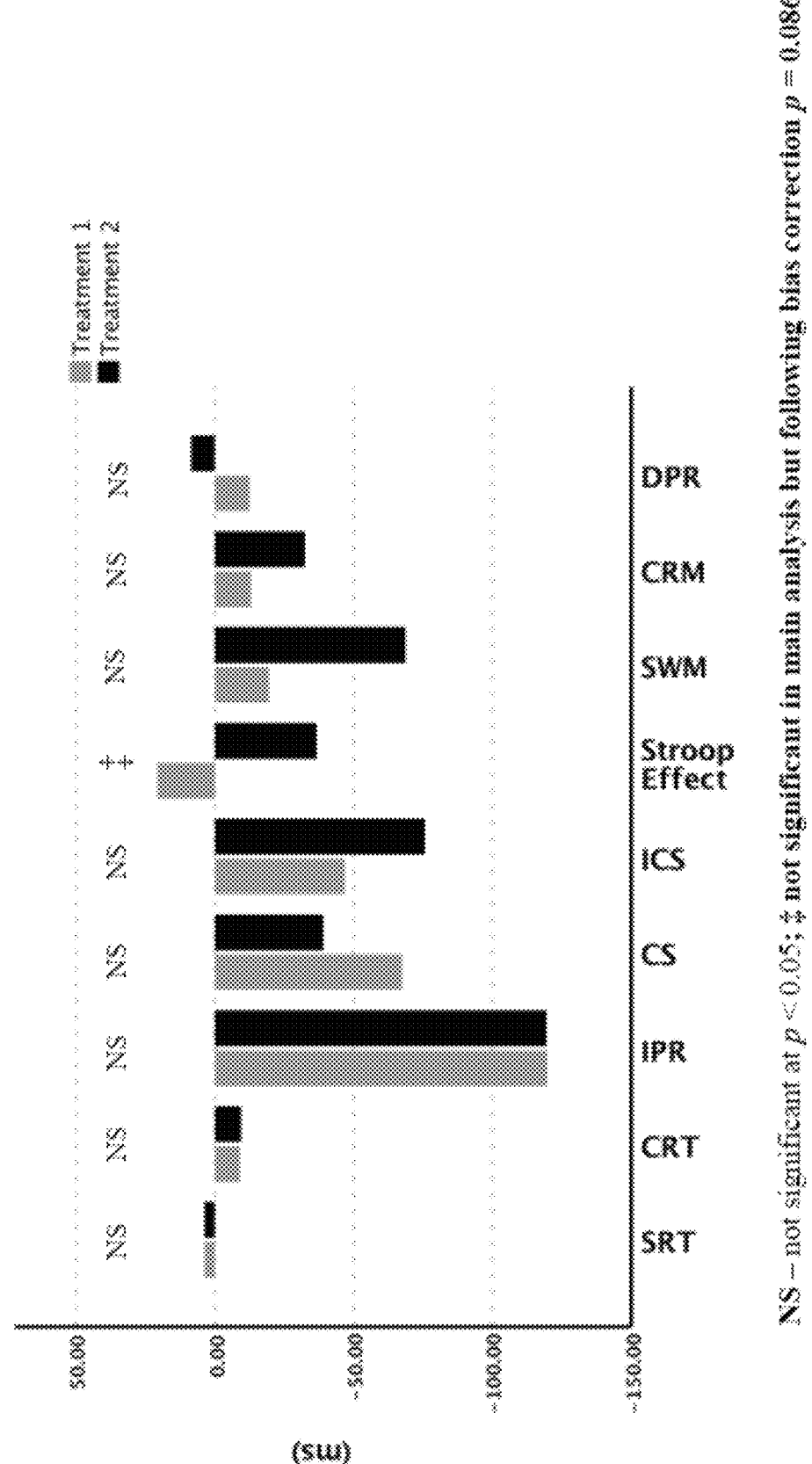

FIG. 4 shows changes in the Swinburne University Computerised Cognitive Ageing Battery (SUCCAB) task response times following administration of Treatment 1 (placebo) or Treatment 2 (DHA-containing dose). SUCCAB task measures were simple reaction time (SRT), choice reaction time (CRT), immediate picture recognition (IPR) (immediate recognition memory), congruent stroop (CS), incongruent stroop (ICS), stroop effect, spatial working memory (SWM), contextual recognition memory (CRM) and delayed picture recognition (DPR) (delayed recognition memory).

DETAILED DESCRIPTION

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the terms "a" and "an" refer to one or to more than one (i.e. to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

In the context of this specification, reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein, the term "and/or" means "and" or "or" or both.

In the context of this specification, the term "acutely" is understood to mean a relatively rapid onset of a beneficial physiological or cognitive effect. An acute effect is distinct from a chronic effect which is an effect that occurs over a longer time period. Those skilled in the art readily understand and appreciate the difference between an acute effect and a chronic effect. In the context of the present disclosure a beneficial acute effect is observed over a period of minutes or hours.

In the context of this specification, the term "improving/ enhancing" as it relates to cognitive performance is understood to mean that cognitive performance is superior or better in a subject who is administered one or more LCPU-FAs when compared to cognitive performance of the subject in the absence of an administered LCPUFA. Improvement/ enhancement may be assessed by comparing the cognitive performance of a subject who is administered one or more LCPUFAs with the cognitive performance of the same subject in the absence of LCPUFAs. The improvement/ enhancement may be qualitative or quantitative. The improvement/enhancement may be at least or about 5%, 10%, 15%, 20%, 25%, 30%, 35%, 40%, 45%, 50%, 55%, 60%, 65%, 70%, 75%, 80%, 85%, 90% or 95%.

As used herein the terms "treating", "treatment", "treating", "reduce", "reducing", "prevent" "preventing" and "prevention" and the like refer to any and all applications which remedy, or otherwise hinder, retard, or reverse the progression of, a condition or disorder or at least one symptom of a condition or disorder, including reducing the severity of a condition or disorder. Thus, the terms "treat", "treating", "treatment", do not necessarily imply that a subject is treated until complete recovery from a condition or disorder. Similarly, the terms "prevent", "preventing", "prevention" and the like refer to any and all applications that prevent the establishment of a condition or disorder or otherwise delay the onset of a condition or disorder.

In the context of this specification, the term "cognitive performance" is understood to mean the ability or capacity of a subject in carrying out a task that involves or requires cognition, such as for example thinking, reasoning, understanding, problem solving and/or decision making.

In the context of this specification, the term "improving/ enhancing" as it relates to cardiovascular function is understood to mean that cardiovascular function is superior or better in a subject who is administered one or more LCPU-FAs when compared to cardiovascular function of the subject in the absence of an administered LCPUFA. Improvement/enhancement may be assessed by comparing the cardiovascular function of a subject who is administered a LCPUFA with the cardiovascular function of the same subject in the absence of an administered LCPUFA. The improvement/enhancement may be qualitative or quantitative. The improvement/enhancement may be at least or about 5%, 10%, 15%, 20%, 25%, 30%, 35%, 40%, 45%, 50%, 55%, 60%, 65%, 70%, 75%, 80%, 85%, 90% or 95%.

The present inventors have conducted a double-blind placebo controlled study examining the acute effects of a dose (4 g) of docosahexaenoic acid (DHA) on participants' cardiovascular activity and performance in a mentally effortful cognitive task (a cognitive demand battery) before and after administration of the DHA. As exemplified herein, the study demonstrated acute improvements (4 hours) in numerous blood pressure measures following administration of the dose of DHA and concurrent with increase in blood levels of DHA, relative to a placebo. Various cognitive test response times were also reduced on an acute timescale (4 hours) following administration of the DHA.

In one aspect the present invention provides a method for acutely improving/enhancing cognitive performance and/or cardiovascular function in a human subject, the method comprising administration to the subject of one or more LCPUFAs.

The present disclosure also provides a method for treating or preventing dementia, for example by way of acutely improving/enhancing cognitive performance and/or cardiovascular function in a human subject, for example by acutely reducing pulse pressure in the subject.

The methods of the present disclosure comprise administration of one or more LCPUFAs to a subject. The LCPUFA may be used in any available form, for example as one or more oil(s) comprising the one or more LCPUFAs.

The oil(s) may be naturally occurring or naturally derived, or may be synthetic from genetically modified or non-genetically modified source. The oils may be a naturally derived oil which has been further modified , for example a re-esterified oil, for example a re-esterified marine oil concentrate, for example as used in Driphorm® HiDHA 360 (NuMega Ingredients, Australia). In the context of the present disclosure "naturally occurring" and "naturally derived" includes oils and lipid compositions that may be extracted from a natural source such as the organisms listed herein, or that may be derived from or modified from an oil or one or more lipids found in such natural sources. The skilled person will appreciate that scope of the present disclosure is not limited by reference to the identity or source of the one or more LCPUFAs or oil(s) comprising the one or more LCPUFAs.

Exemplary oils that are, or can be modified to be LCPUFA-containing or LCPUFA-rich, include oils from marine organisms such as, for example, crustaceans such as hill, molluscs such as oysters, and fish such as tuna, salmon, trout, sardines, mackerel, sea bass, menhaden, herring, pilchards, kipper, eel or whitebait. The oil may be from the roe of one or marine organisms such as those listed herein. In exemplary embodiments, the oil is or comprises tuna oil, hill oil or a lipid extract from fish roe.

Other exemplary oils that are, or may be modified to be LCPUFA-containing or LCPUFA-rich, include oils from plant sources and single cell organism sources. Plant sources include, but are not limited to, flaxseed, walnuts, sunflower seeds, canola, safflower, soy, wheat germ, corn and leafy green plants such as kale, spinach and parsley. Single cell organism sources include algae, fungi and bacteria.

Any of the above-mentioned oils may, according to some embodiments, be used in their concentrated form.

The LCPUFAs typically comprise one or more omega-3 fatty acids and/or one or more omega-6 fatty acids, or mixtures thereof. The fatty acids may include docosapentaenoic acid (DHA), Arachidonic acid (AA), eicosapentaenoic acid (EPA), DPA and/or stearidonic acid (SDA), or mixtures thereof. In particular embodiments, the LCPUFAs comprise omega-3 fatty acids. In one embodiment, the fatty acids comprise DHA and EPA.

The LCPUFAs may be provided in a microencapsulated form. For example, a LCPUFA-containing oil may be microencapsulated by an encapsulant comprising one or more low molecular weight proteins or an emulsifier comprising low molecular weight proteins fractions. Such microencapsulation may provide various advantages, such as improving the oxidative stability of LCPUFA-rich oils. By way of example only, LCPUFAs may be encapsulated as described in PCT applications PCT/AU2018/050339, PCT/AU2018/050384 or PCT/AU2019/050763, the contents of which are incorporated herein by reference.

A commercially available form of LCPUFAs is Driphorm HiDHA 360 powder, available from Nu-Mega Ingredients, which is a source of DHA which is microencapsulated in a matrix of milk protein, sugars and antioxidants.

LCPUFAs may be administered in accordance with the present disclosure in the form of pharmaceutical compositions, which compositions may comprise one or more pharmaceutically acceptable carriers, excipients or diluents. Such compositions may be administered to subjects by any by any convenient or suitable route such as, for example by parenteral, oral, or topical routes. Typically, the compositions are administered via the oral route.

Pharmaceutical compositions for use in accordance with the present invention may conveniently be prepared by methods well known in the art of pharmacy. All methods include the step of bringing one or more LCPUFAs or LCPUFA-containing oils into association with one or more pharmaceutically acceptable carrier, diluent and/or excipient. In general, the compositions may be prepared by uniformly and intimately bringing into association one or more LCPUFAs or LCPUFA-containing oils with a liquid carrier or finely divided solid carrier.

Examples of pharmaceutically acceptable carriers, diluents and excipients include but are not limited to: demineralised or distilled water, saline solution, vegetable-based oils such as peanut oil, safflower oil, olive oil, cottonseed oil, maize oil and sesame oil, volatile silicones, mineral oils, cellulose derivatives such as methyl cellulose, ethyl cellulose, carboxymethylcellulose, sodium carboxymethylcellulose or hydroxypropylmethylcellulose, fatty acid esters, polyvinylpyrrodone, carrageenan and gums. Typically the carriers, diluents and excipients will form from 5% to 99.9% by weight of the compositions. Carriers, diluents and excipients must, of course, be acceptable in the sense of being compatible with any other components of the composition and must not be deleterious to the subject.

Compositions contemplated by the present disclosure may further comprise additional components, for example, antioxidants, anti-caking agents, flavouring agents, colouring agents, vitamins, minerals, amino acids, chelating agents and the like.

Suitable antioxidants are well known to those skilled in the art, and may be water soluble or oil soluble. Suitable water soluble antioxidants include, for example, sodium ascorbate, calcium ascorbate, potassium ascorbate, ascorbic acid, glutathione, lipoic acid and uric acid. In an embodiment the water soluble antioxidant may be present in the composition in a range of about 0-10% wt/wt of the total composition. Suitable oil soluble antioxidants include, for example, tocopherols, ascorbyl palmitate, tocotrienols, phenols, polyphenols and the like. In an embodiment the oil soluble antioxidant is present in the oil phase in a range of about 0-10% wt/wt of the total composition.

Anti-caking agents that are compatible with the compositions of the present disclosure will be well known amongst those skilled in the art and include calcium phosphates, such as tricalcium phosphate and carbonates, such as calcium and magnesium carbonate and silicon dioxide The compositions may further comprise one or more low molecular weight emulsifiers. Suitable low molecular weight emulsifiers include, for example, mono- and di-glycerides, lecithin and sorbitan esters. Other suitable low molecular weight emulsifiers will be well known to those skilled in the art. The low molecular weight emulsifier may be present in an amount between about 0.1% and 3% of the total weight of the composition, or in an amount between about 0.1% and about 2%, or in an amount between about 0.1% and 0.5%, or in an amount between about 0.1% and 0.3%, of the total weight of the composition. For example, the low molecular weight emulsifier may be present in an amount of about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9% or 2% of the total weight of the composition.

The LCPUFAs or composition thereof may be in liquid or solid form, and may be consumed as such (for example in the form of a syrup or other suitable liquid, or as capsules or other suitable solid form). Alternatively, the LCPUFAs or compositions thereof may be incorporated into food or beverage products.

Alternatively, LCPUFAs or LCPUFA-containing oils may be administered neat, i.e. in the absence of a carrier, excipient and/or diluent.

LCPUFAs or compositions thereof suitable for oral administration may be presented as discrete units, such as for example gelatine or HPMC capsules, cachets or tablets, each containing a predetermined amount of extract.

When provided in the form of a capsule, the LCPUFAs may be formulated with one or more pharmaceutically acceptable carriers such as starch, lactose, microcrystalline cellulose, silicon dioxide and/or a cyclic oligosaccharide such as cyclodextrin. Additional ingredients may include lubricants such as magnesium stearate and/or calcium stearate.

Tablets may be prepared by compression or moulding, optionally with one or more accessory ingredients. Compressed tablets may be prepared by compressing in a suitable machine the LCPUFAs or composition thereof in a free-flowing form such as a powder or granules, optionally mixed with a binder, lubricant (for example magnesium stearate or calcium stearate), inert diluent or a surface active/dispersing agent. Moulded tablets may be made by moulding a mixture of the powdered LCPUFA or composition thereof moistened with an inert liquid diluent, in a suitable machine. The tablets may optionally be coated, for example, with an enteric coating and may be formulated so as to provide slow or controlled release of the LCPUFAs therein.

Acute effects of the LCPUFAs may be apparent, for example, within 6 hours, within 5 hours, within 4 hours, or within 3 hours.

The LCPUFAs may be administered in accordance with the present disclosure to a subject with impaired memory. The LCPUFAs may be administered in accordance with the present disclosure to a subject prior to, during, and/or after the subject being mentally stressed, mentally fatigued and/or cognitively challenged.

In the context of this specification, the term "cognitively challenged" is understood to mean that the subject is faced with a task or problem that involves or requires cognition, such as for example recall, memory, thinking, reasoning, understanding, problem solving and/or decision making, in particular a difficult or complex task or problem that may give rise to mental stress or mental fatigue in the subject.

In the context of this specification, the term "mentally stressed" is understood to mean strain or tension associated with recall, memory, thinking, reasoning, understanding, problem solving and/or decision making. In the context of this specification the term "mentally fatigued" is understood to mean tiredness or exhaustion associated with recall, memory, thinking, reasoning, understanding, problem solving and/or decision making.

The LCPUFAs may be administered in accordance with the present disclosure to a subject with elevated blood pressure, for example due to a cardiovascular condition or other condition or disease, medication, or stress. The high blood pressure may be transient or chronic. The LCPUFAs may be administered in accordance with the present disclosure to a subject prior to, during, and/or after the subject being cardiovascularly stressed. In the context of this specification, the term "cardiovascularly stressed" refers to a subject having high blood pressure, or being prone to the development of high blood pressure, either transiently, acutely or chronically. For example, a cardiovascular stress may take the form of a task, activity, situation, circumstance or environment which results in an increase in blood pressure, transiently and/or acutely.

In some embodiments, the LCPUFAs are administered at least 1 minute, at least 5 minutes, at least 10 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, at least 150 minutes, or at least 180 minutes prior to the subject being mentally stressed, mentally fatigued and/or cognitively challenged, or cardiovascularly stressed. In other embodiments, the LCPUFAs are administered about 5 minutes to about 5 hours prior to, or about 2 hours to about 5 hours prior to, or about 3 hours to about 5 hours prior to, or about 3 hours to about 4 hours prior to, or about 5 minutes to about 4 hours prior to, about 5 minutes to about 3 hours prior to, or about 15 minutes to about 3 hours prior to, or about 30 minutes to about 3 hours prior to, or about 1 hour to about 3 hours prior to, or about 2 hours to about 3 hours prior to the subject being mentally stressed, mentally fatigued and/or cognitively challenged, or cardiovascularly stressed. In further embodiments, the LCPUFAs are administered up to 1 minute, up to 5 minutes, up to 10 minutes, up to 20 minutes, up to 30 minutes, up to 40 minutes, up to 50 minutes, up to 60 minutes, up to 70 minutes, up to 80 minutes, up to 90 minutes, up to 100 minutes, up to 110 minutes, up to 120 minutes, up to 130 minutes, up to 140 minutes, up to 150 minutes, up to 180 minutes, up to 210 minutes, up to 240 minutes or up to 300 minutes prior to the subject being mentally stressed, mentally fatigued and/or cognitively challenged, or cardiovascularly stressed.

The LCPUFAs may be administered in an amount of at least 50 mg, for example at least 100 mg, for example at least 500 mg, for example at least 1 g. The LCPUFAs may be administered in an amount between about 50 mg and about 10.0 g, or in an amount between about 100 mg and about 10.0 g, or in an amount between about 0.5 g and about 6 g, or in an amount between about 1 g and about 6 g, or in an amount between about 2 g and about 6 g, or in an amount between about 3 g and about 6 g, or in an amount between about 3 g and about 5 g, or in an amount of about 4g.

The LCPUFAs may be administered as a single dose or alternatively as multiple doses sequentially.

In a further aspect, the present invention provides a use of one or more LCPUFAs in the manufacture of a medicament for acutely improving/enhancing cardiovascular function and/or cognitive performance in a subject.

The present disclosure further provides use of one or more LCPUFAs in the manufacture of a medicament for treating or preventing dementia, the treatment or prevention being for example by way of acutely improving/enhancing cognitive performance and/or cardiovascular function in a human subject, for example by acutely reducing pulse pressure in the subject.

In some embodiments, the medicament may be administered at least 5 minutes, at least 10 minutes, at least 20 minutes, at least 30 minutes, at least 40 minutes, at least 50 minutes, at least 60 minutes, at least 70 minutes, at least 80 minutes, at least 90 minutes, at least 100 minutes, at least 110 minutes, at least 120 minutes, at least 130 minutes, at least 140 minutes, at least 150 minutes, at least 180 minutes, at least 210 minutes, at least 240 minutes or at least 300 minutes prior to commencement of a test, examination or other activity involving cognition, or prior to exercise, physical exertion or exposure to stress. In other embodiments, the extract is administered about 5 minutes to about 3 hours prior to, or about 2 hours to about 5 hours prior to, or about 3 hours to about 5 hours prior to, or about 3 hours to about 4 hours prior to, or about 15 minutes to about 3 hours prior to, or about 30 minutes to about 3 hours prior to, or about 1 hour to about 3 hours prior to, or about 2 hours to about 3 hours prior to commencement of a test, examination or other activity involving cognition, or prior to exercise, physical exertion or exposure to stress. In further embodiments, the extract is administered up to 1 minute, up to 5 minutes, up to 10 minutes, up to 20 minutes, up to 30 minutes, up to 40 minutes, up to 50 minutes, up to 60 minutes, up to 70 minutes, up to 80 minutes, up to 90 minutes, up to 100 minutes, up to 100 minutes, up to 120 minutes, up to 130 minutes, up to 140 minutes, up to 150 minutes, up to 180 minutes, up to 210 minutes, up to 240 minutes or up to 300 minutes prior to commencement of a test, examination or other activity involving cognition, or prior to exercise, physical exertion or exposure to stress.

In an embodiment, the medicament comprises an amount of LCPUFAs of at least 50 mg, for example at least 100 mg, for example at least 500 mg, for example at least 1 g. The medicament may comprise an amount of LCPUFAs of between about 50 mg and about 10.0 g, or in an amount between about 100 mg and about 10.0 g, or in an amount between about 0.5 g and about 6 g, or in an amount between about 1 g and about 6 g, or in an amount between about 2 g and about 6 g, or in an amount between about 3 g and about 6 g, or in an amount between about 3 g and about 5 g, or in an amount of about 4g.

The medicament may be administered as a single dose or alternatively as multiple doses sequentially.

In another aspect the present invention provides use of one or more LCPUFAs for acutely improving/enhancing cardiovascular function and/or cognitive performance in a subject.

The present disclosure provides use of one or more LCPUFAs for the treatment or prevention of dementia, for example by way of acutely improving/enhancing cardiovascular function and/or cognitive performance in a human subject, for example by acutely reducing pulse pressure in the subject.

In a further aspect the present invention provides one or more LCPUFAs for use in a method of acutely improving/enhancing cardiovascular function and/or cognitive performance in a subject.

The present disclosure provides one or more LCPUFAs for use in a method of treating or preventing dementia, for example by way of acutely improving/enhancing cardiovascular function and/or cognitive performance in a human subject, for example by acutely reducing pulse pressure in the subject.

The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

EXAMPLES

The invention will now be described in more detail, by way of illustration only, with respect to the following examples. The examples are intended to serve to illustrate this invention and should in no way be construed as limiting the generality of the disclosure of the description throughout this specification.

Example 1

Study Design

A randomised, double-blind, placebo-controlled, cross-over trial was carried out to investigate the acute effects of a dose of docosahexaenoic acid (DHA)-rich powder included in a meal on cognitive performance and cardiovascular function.

The DHA-containing treatment ("DHA treatment") was Driphorm HiDHA 360, a DHA-rich spray dried powder containing concentrated omega-3 marine oil, microencapsulated in a matrix of milk protein, sugars and antioxidants. Participants were administered 12g of powder, mixed with a milk drink or vanilla yoghurt, in order to receive a 4 g dose of DHA.

The placebo treatment was a spray-dried powder matched in appearance to the DHA treatment. The placebo powder contained 58% food grade high oleic sunflower oil ("Sunola oil"), microencapsulated in a matrix of milk protein, sugars and antioxidants. The powder was mixed with the same milk drink or yoghurt as the active treatment. 1 drop of fish oil was also added to give the placebo a similar taste and smell as the active treatment. This small amount of fish oil does not provide a high enough dose for any cognitive effects to be apparent.

40-60 year old males free of any neurological, psychiatric conditions, metabolic disorders and cardiovascular disease, not taking any fish oil supplements or other cognitive enhancing dietary supplements, with no allergies to seafood, bread or milk products, and not consuming more than one serve per week of oily fish were recruited for the study. To be eligible to participate, participants must not have been taking any medications, herbal extracts, illicit drugs or vitamin supplements which might reasonably be expected to interfere with mood and cognition for 4 weeks prior to (and duration of) the study. If participants took any medications/treatments for benign conditions (e.g. allergy medication) during the study period, they were asked to refrain from taking this medication for 5 days before, and for the duration of, the testing days.

Within 14 days of a screening and practice visit to the clinic, a further visit (visit 1) was carried out in which subjects were administered with a study dose of either the DHA treatment or the placebo. On a second visit to the clinic following visit 1 (visit 2), the other of a dose of the DHA treatment or the placebo was administered to the subjects. Subjects were asked to avoid eating from 10 pm the night before the visit and refrain from: consuming caffeine for 10 hours prior to and during the study visit; consuming alcohol for 12 hours prior to and during the study visit; and participating in vigorous physical activity for 12 hours prior to and during each study visit (not including the screening visit). Participants were also asked to consume a low-fat meal the night before their testing sessions, such as chicken and vegetables.

On each of visit 1 and visit 2, subjects provided a fasting blood sample and cardiovascular assessment (SphygmoCor XCEL®), and ate a standardised meal. Subjects then completed the cognitive assessments (Swinburne University Computerised Cognitive Ageing Battery (SUCCAB)). These assessments are discussed in further detail below.

After completing the above tasks, subjects were administered the study dose. Once the treatment was consumed, participants had a 3.5-4 hour break, during which time a portable blood pressure monitor was worn on the upper arm to allow period cardiovascular assessments during the break.

After the break, a second blood sample was obtained, and the cognitive and cardiovascular assessments were repeated in order to assess the acute effect of the treatment. A symptoms checklist was administered at the end of the session and subjects were questioned non-specifically for any adverse events.

All participants were assigned a participant number. All participants received both treatments on separate study days. Counterbalancing of treatments was determined by random allocation. All eligible participants were assigned treatments using a computer generated random number generator by a disinterested third party. Each eligible participant was assigned a treatment number which was the allocated treatment for that individual. Randomization codes were kept in a password protected computer file.

Participants were required to consume the study dose within 5-10 minutes of administration. Participants were asked not to leave the study site until the treatment had been consumed.

Data from a total of 25 subjects were available for analysis. At screening no participants had a brachial blood pressure (systolic/diastolic) greater than 160/90 mmHg. Testing of further participants was interrupted due to the COVID-19 pandemic and subsequent restrictions to research (i.e. shutdown of the university, community stay at home order & social distancing), but at least six further individuals have been identified which satisfy eligibility criteria and have been added to a waiting list to begin the trail once research is permitted to resume.

Example 2

Overview of Statistical Analyses

All statistical tests were performed two tailed at the 5% significance level and performed using the IBM Statistical Package for the Social Sciences, version 27 (SPSS v.27) or Microsoft® Excel. Prior to statistical analysis, all plasma fatty acid, cardiovascular and cognitive data was screened for invalid data points. For cognitive data, any response accuracy which fell below that expected by chance (i.e. the poorest possible result if participants were to make the same response to all stimuli in a task) was considered invalid (response time data for these participants was subsequently excluded from analysis). In addition, any data considered to be biologically implausible was deemed invalid. All invalid data was marked as 'missing' and excluded from analysis. The removal of invalid data was the only method of bias reduction performed prior to the initial analyses.

Statistical analysis, and in particular the determination of interaction p-values, was used to evaluate the change over time of each treatment (placebo and DHA treatment) and the differences between the two treatments. Cognition studies often reveal improvements in treatment and placebo groups over time due to practice. Thus, interaction p values were calculated to assess the effects of the DHA treatment over time above and beyond the effects of the placebo. Examination of treatment effects was performed using two-way repeated measures ANOVA. This analysis method only utilises complete data sets, so any participant with an incomplete data set (e.g. dependent variables with missing data) was excluded from analysis. Differential treatment effects were considered significant if the interaction effect reached the $p<0.05$ (two tailed) level, or trending if at or below $p<0.10$. Following initial analysis with all available data, the two-way repeated measures ANOVAs were replicated following the application of standard bias reduction methods (Field (2018), The Beast of Bias. In A. P. Field (5th.

Ed), *Discovering statistics using IBM SPSS statistics* (pp. 225-280). Thousand Oaks, California: SAGE Publications). These methods included identification and removal of univariate outliers (defined as Z score greater than 3.29 which are disconnected from the data spread), as well as transformation of any data deemed significantly skewed. Any participant with a univariate outlier (at any condition level of the dependent variable i.e. Treatment 1 or Treatment 2, pre-dose or post-dose) was subsequently excluded from analysis of that particular dependent variable. Data was considered significantly skewed ($p<0.05$ level) if the resulting value of skewness/skewness error (for residuals) was outside the $-1.96$ to $1.96$ range (Kim, (2013), Statistical notes for clinical researchers: assessing normal distribution (2) using skewness and kurtosis. *Restorative Dentistry & Endodontics*, 38, 52-54). In the case of skewed data, all conditions (i.e. levels) of the dependent variable were transformed in the same manner using the appropriate transformation to ameliorate the skew. Due to the strength of effects on plasma fatty acid (as discussed in Example 3 below), plasma fatty acid analyses were not repeated following bias reduction.

Example 3

Omega-3 Plasma Concentrations

In order to detect any changes in omega-3 status after supplementation, plasma omega-3 fatty acid analysis was conducted twice at both study visits. Participants gave two blood samples, one prior to supplementation, and the other 4 hours after supplementation in order to determine acute omega-3 effects in the blood.

Blood was drawn (10 ml) via venepuncture on each testing day prior to pre-dose and post-dose testing. The samples were then spun in a refrigerated centrifuge and spun at 4000 rpm for five minutes at 4° C., after which two 1 ml samples of plasma were extracted, labelled, and stored in a dedicated research freezer at $-80$° C. before analysis. The concentrations of omega-3 and omega-6 fatty acids were reported in mg/L plasma. The ratios of total omega-3, DHA or EPA, to total omega-6 fatty acids, or AA were calculated by dividing the omega-3 value by the omega-6 value (e.g. DHA:AA ratio=Total DHA/Total AA). Following the exclusion of incomplete and ambiguous data sets, 18 complete datasets were available for analysis.

All valid data was utilised for analysis; given the strength of effects, the plasma fatty acid analyses were not repeated following removal of outliers and/or data transformation.

Figure 1:
FIG. 1 shows the pre-dose to post-dose change in plasma fatty acid concentrations for Treatment 1 (placebo) and Treatment 2 (DHA-containing dose).
Figure 2:
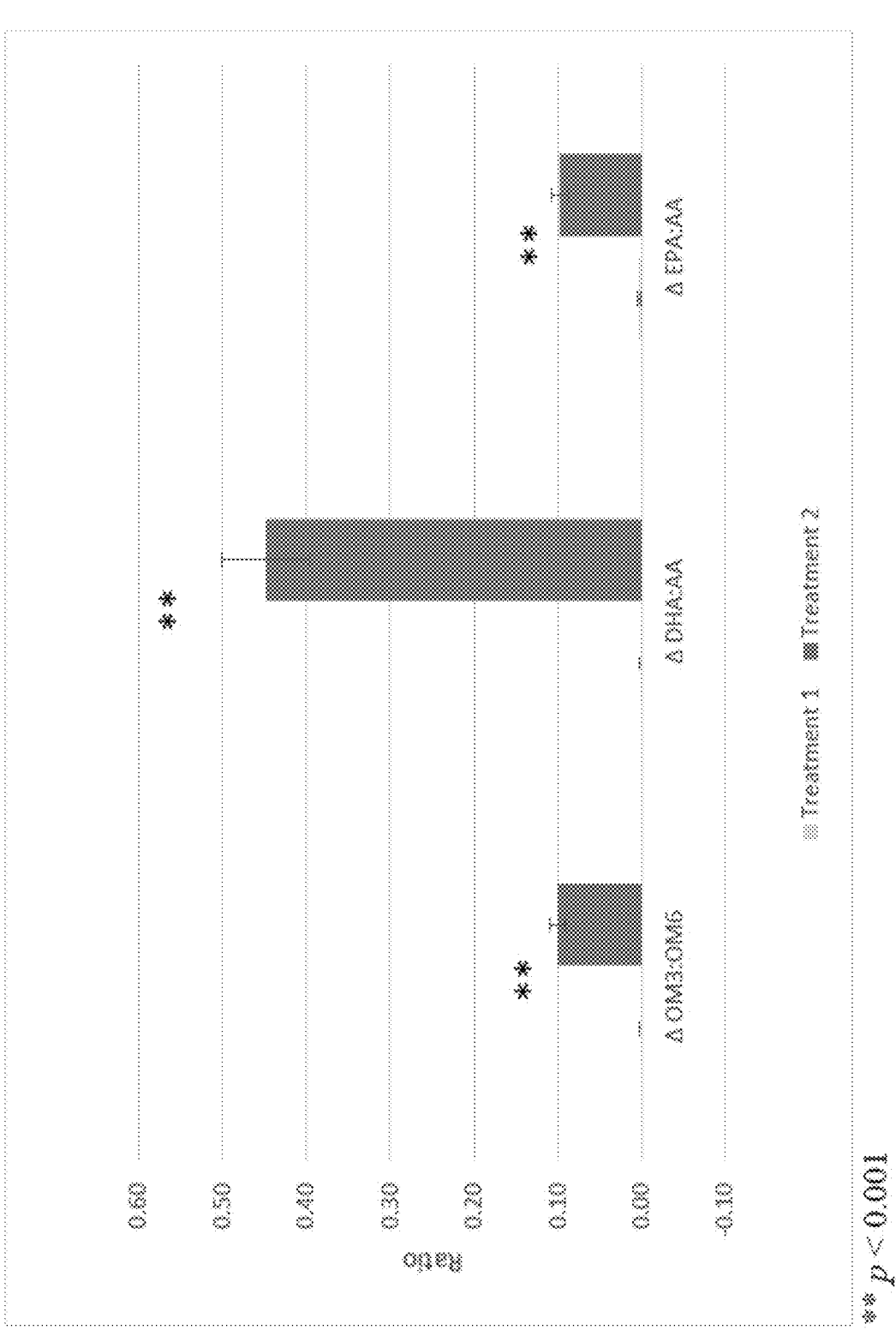
FIG. 2 shows the pre-dose to post-dose change in plasma fatty acid ratios for Treatment 1 (placebo) and Treatment 2 (DHA-containing dose)..

The extent to which plasma fatty acid concentrations or ratios changed from pre-dose to post-dose following consumption of Treatment 1 and Treatment 2 is displayed in FIG. 1 and FIG. 2, respectively; the significance level for these differences is given in the figure. Descriptive statistics for all plasma fatty acid concentrations or ratios are presented in Table 1 below.

TABLE 1

| Descriptive Statistics for Plasma Fatty Acids Concentrations & Ratios. | | |
|---|---|---|
| Assessment | Mean | SD |
| Treatment 1 - Pre-dose | | |
| Total Plasma Omega-3 | 140.09 | 37.61 |
| Plasma DHA | 61.56 | 15.59 |
| Plasma EPA | 31.77 | 12.25 |
| Total Plasma Omega-6 | 1237.20 | 218.53 |

TABLE 1-continued

| Descriptive Statistics for Plasma Fatty Acids Concentrations & Ratios. | | |
| --- | --- | --- |
| Assessment | Mean | SD |
| Plasma AA | 214.11 | 47.86 |
| Total Plasma Omega-3:Omega-6 Ratio | 0.112 | 0.017 |
| Plasma DHA:AA Ratio | 0.295 | 0.078 |
| Plasma EPA:AA Ratio | 0.149 | 0.047 |
| Treatment 2 - Pre-dose | | |
| Total Plasma Omega-3 | 129.34 | 30.88 |
| Plasma DHA | 58.09 | 15.13 |
| Plasma EPA | 27.02 | 8.10 |
| Total Plasma Omega-6 | 1254.07 | 265.95 |
| Plasma AA | 214.66 | 52.23 |
| Total Plasma Omega-3:Omega-6 Ratio | 0.104 | 0.019 |
| Plasma DHA:AA Ratio | 0.276 | 0.061 |
| Plasma EPA:AA Ratio | 0.127 | 0.032 |
| Treatment 1 - Post-dose | | |
| Total Plasma Omega-3 | 163.03 | 49.26 |
| Plasma DHA | 66.77 | 18.03 |
| Plasma EPA | 35.25 | 16.87 |
| Total Plasma Omega-6 | 1429.52 | 313.63 |
| Plasma AA | 231.28 | 57.19 |
| Total Plasma Omega-3:Omega-6 Ratio | 0.113 | 0.018 |
| Plasma DHA:AA Ratio | 0.297 | 0.077 |
| Plasma EPA:AA Ratio | 0.151 | 0.050 |
| Treatment 2 - Post-dose | | |
| Total Plasma Omega-3 | 266.28 | 91.45 |
| Plasma DHA | 152.16 | 53.19 |
| Plasma EPA | 47.69 | 12.30 |
| Total Plasma Omega-6 | 1306.05 | 243.54 |
| Plasma AA | 218.53 | 49.13 |
| Total Plasma Omega-3:Omega-6 Ratio | 0.202 | 0.049 |
| Plasma DHA:AA Ratio | 0.716 | 0.246 |
| Plasma EPA:AA Ratio | 0.222 | 0.055 |

Note:

N for all measures is 18. Total Plasma Omega-3, Plasma DHA, Plasma EPA, Plasma Omega-6, and Plasma AA are measured in mg/L Plasma.

As shown in FIG. 1, significant differential treatment effects were evident for all measures examined. Specifically, Treatment 2 appeared to increase the concentrations of Total Plasma Omega-3, Plasma DHA, and Plasma EPA to a larger degree than Treatment 1. Treatment 2 also facilitated a greater increase in Total Omega-3:Omega-6, DHA:AA, and EPA:AA ratios. Conversely, Treatment 1 facilitated greater increases in Total Plasma Omega-6, thought to be due to the presence of omega-6 fatty acids in the sunflower oil used in the placebo.

DHA treatment carry over effects were examined using the method in Wellek & Blettner, 2012 (*Deutsches Arzteblatt International* 109:276-281). The method examines whether the washout period between administrations was adequate, i.e. whether the treatment at visit 1 impacts visit 2 results. The method only used whole data sets. According to the method in Wellek & Blettner, t-test scores were calculated for changes in LCPUFA concentrations/ratios following administration of the dose and the placebo. It was determined that, for there to be significant carry over effects at the p<0.05 level (two tailed), the resulting t-test score would have to exceed 2.26 (or −2.26). Resulting t-test scores fell within the range 0.13-1.41, indicating that there were no significant carry over effects, i.e. that the treatment issued at visit 1 did not impact the results obtained at visit 2.

Example 4

Acute Effect of DHA Treatment on Cardiovascular Function

A SphygmoCor® XCEL device (AtCor Medical, Sydney, Australia) was used to conduct non-invasive assessment of brachial blood pressure as well as aortic blood pressure at the beginning of pre-dose and post-dose testing sessions. This device adheres to the necessary Australian safety standards and is commonly used to assess and manage cardiovascular health. Brachial blood pressure was calculated with the participant supine and following a five minute rest period. An appropriately sized blood pressure cuff was placed around the participants arm. Following the rest period, the SphygmoCor XCEL device automatically inflates and deflates the cuff in order to measure brachial blood pressure. Three measurements were taken in succession with the average used in statistical analysis.

The SphygmoCor® XCEL device provides data for brachial systolic and diastolic blood pressures (millimetres mercury, mmHg). Once the SphygmoCor XCEL device had automatically calculated brachial blood pressure, the blood pressure cuff immediately inflated a final time. Upon final inflation, the SphygmoCor XCEL device automatically and non-invasively derived the aortic pressure waveform using a mathematical transfer function applied to the brachial waveform. From this aortic pressure waveform, aortic pressure was automatically calculated by the software. Various measures of arterial stiffness (i.e. augmented pressure & augmentation index) were also calculated using a mathematical transfer function applied to the brachial waveform. Brachial and aortic pulse pressures were calculated in accordance with Pase et al. (2013) (Blood Pressure and Cognitive Function: The Role of Central Aortic and Brachial Pressures. Psychological Science, 24, 2173-2181) as follows:

$$\text{Brachial/Aortic Pulse Pressure} = \text{Systolic Pressure} - \text{Diastolic Pressure}$$

Brachial and aortic mean arterial blood pressures (MABP) were also calculated. MABP is a measure of perfusion pressure (i.e. the pressure applied to sensitive blood vessels in organs). MABP was $$\text{Brachial/Aortic } MABP = \frac{(\text{Diastolic Pressure} \times 2) + (\text{Systolic Pressure})}{3}$$

calculated in accordance with Pase et al. (2013) as follows:

Carotid-femoral pulse wave velocity (cf-PWV) was also measured, and is used to assess aortic elasticity or stiffness (Mattace-Raso et al. (2010) (Determinants of Pulse Wave Velocity in Healthy People and in the Presence of Cardiovascular Risk Factors: 'Establishing Normal and Reference Values'. *European Heart Journal*, 31, 2338-2350). Typically, multiple (at least 2) recordings of cf-PWV were obtained during a testing session. However, the value for cf-PWV used in the analysis was the test result demonstrating the lowest variance (i.e. standard deviation given to one decimal place—manufacturer's specification). If two cf-PWV recordings were characterized by the same variance, the average of the recordings was calculated and used instead.

Statistics for each measure of cardiovascular function assessed are provided in Table 2 below. The extent to which various cardiac pressure values changed from the pre-dose to post-dose following consumption of Treatment 1 and

15

Figure 3:
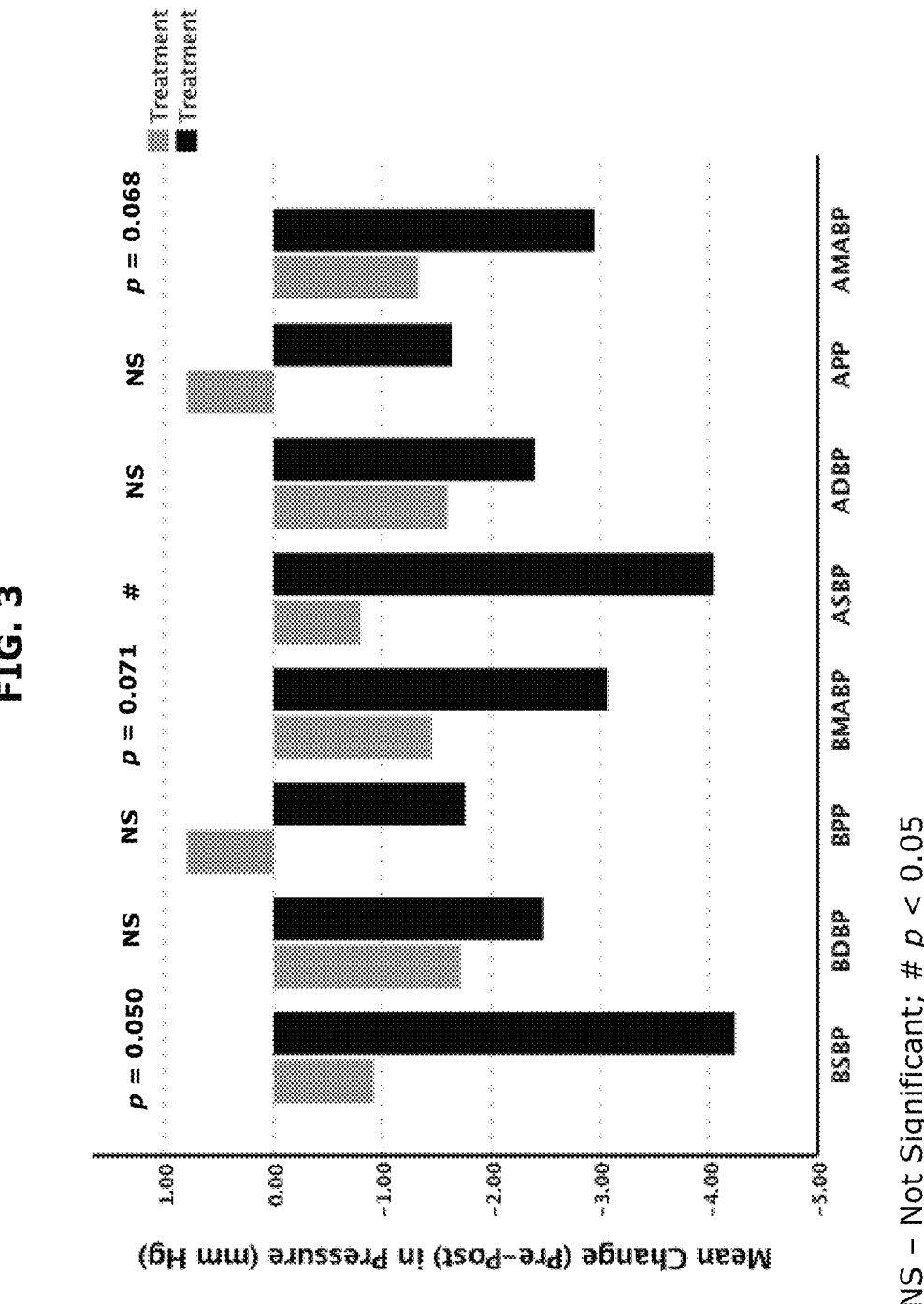
FIG. 3 shows changes in brachial systolic blood pressure (BSBP), brachial diastolic blood pressure (BDBP), brachial pulse pressure (BPP), brachial mean arterial blood pressure (BMABP), aortic systolic blood pressure (ASBP), aortic diastolic blood pressure (ADBP), aortic pulse pressure (APP) and aortic mean arterial blood pressure (AMABP)

Treatment 2 is displayed in FIG. 3. The significance of these differences is given in the figure.

TABLE 2

Descriptive Statistics for Cardiovascular Function.

| Assessment | Mean | SD | Assessment | Mean | SD |
|---|---|---|---|---|---|
| Treatment 1-Pre-dose | | | Treatment 1-Post-dose | | |
| Brachial Systolic Pressure | 113.88 | 9.87 | Brachial Systolic Pressure | 112.96 | 7.32 |
| Brachial Diastolic Pressure | 71.04 | 6.04 | Brachial Diastolic Pressure | 69.32 | 6.45 |
| Brachial Pulse Pressure | 42.84 | 6.31 | Brachial Pulse Pressure | 43.64 | 4.41 |
| Brachial Mean Arterial Blood Pressure | 85.32 | 6.93 | Brachial Mean Arterial Blood Pressure | 83.87 | 6.43 |
| Aortic Systolic Pressure | 104.80 | 8.68 | Aortic Systolic Pressure | 104.00 | 7.00 |
| Aortic Diastolic Pressure | 71.84 | 6.18 | Aortic Diastolic Pressure | 70.24 | 6.51 |
| Aortic Pulse Pressure | 32.96 | 4.55 | Aortic Pulse Pressure | 33.76 | 4.06 |
| Aortic Mean Arterial Blood Pressure | 82.83 | 6.78 | Aortic Mean Arterial Blood Pressure | 81.49 | 6.40 |
| Heart Rate | 56.88 | 9.19 | Heart Rate | 58.12 | 10.06 |
| Augmentation Pressure | 7.84 | 3.26 | Augmentation Pressure | 7.76 | 3.59 |
| Augmentation Index | 23.28 | 9.04 | Augmentation Index | 22.60 | 9.98 |
| Carotid Femoral Pulse Wave Velocity | 9.99 | 1.03 | Carotid Femoral Pulse Wave Velocity | 9.87 | 0.96 |
| Treatment 2-Pre-dose | | | Treatment 2-Post-dose | | |
| Brachial Systolic Pressure | 115.60 | 10.12 | Brachial Systolic Pressure | 111.36 | 6.68 |
| Brachial Diastolic Pressure | 71.04 | 6.59 | Brachial Diastolic Pressure | 68.56 | 4.14 |
| Brachial Pulse Pressure | 44.56 | 6.63 | Brachial Pulse Pressure | 42.80 | 5.63 |
| Brachial Mean Arterial Blood Pressure | 85.89 | 7.30 | Brachial Mean Arterial Blood Pressure | 82.83 | 4.39 |
| Aortic Systolic Pressure | 106.84 | 9.71 | Aortic Systolic Pressure | 102.80 | 5.84 |
| Aortic Diastolic Pressure | 72.04 | 6.69 | Aortic Diastolic Pressure | 69.64 | 4.08 |
| Aortic Pulse Pressure | 34.80 | 5.32 | Aortic Pulse Pressure | 33.16 | 4.14 |
| Aortic Mean Arterial Blood Pressure | 83.64 | 7.41 | Aortic Mean Arterial Blood Pressure | 80.69 | 4.32 |
| Heart Rate | 57.12 | 8.26 | Heart Rate | 58.00 | 8.15 |
| Augmentation Pressure | 8.80 | 4.44 | Augmentation Pressure | 8.72 | 3.89 |
| Augmentation Index | 24.60 | 10.79 | Augmentation Index | 25.96 | 10.46 |
| Carotid Femoral Pulse Wave Velocity | 9.68 | 0.95 | Carotid Femoral Pulse Wave Velocity | 9.59 | 0.72 |

Note:
All measures except for carotid-femoral pulse wave velocity (cf-PWV) have an N of 25. cf-PWV has an N of 24. All Pressure measurements are given in millimeters mercury (mm Hg); Heart Rate is measured in 'beats per minute"; Augmentation Index is measured as a %; cf-PWV is measured in metres/second.

Observed changes in brachial systolic blood pressure (BSBP), brachial diastolic blood pressure (BDBP), brachial pulse pressure (BPP), brachial mean arterial blood pressure (BMABP), aortic systolic blood pressure (ASBP), aortic diastolic blood pressure (ADBP), aortic pulse pressure (APP) and aortic mean arterial blood pressure (AMABP) are shown in FIG. 3. As seen in FIG. 3, a greater reduction in all blood pressures was observed following administration of the DHA treatment (Treatment 2) than the placebo treatment (Treatment 1). The most marked improvements resulting from DHA treatment, when compared to placebo, were in BSBP (p=0.050), BMABP (p=0.071), ASBP (p<0.05) and AMABP (p=0.068).

A significant differential treatment effect was observed for Aortic Systolic Blood Pressure (ASBP), with Treatment 2 appearing to facilitate a greater reduction in ASBP than Treatment 1. Trends (p<0.10) towards significant differential effects were also evident for Brachial Systolic Blood Pressure (BSBP) (marginal at p=0.050), Brachial Mean Arterial Blood Pressure (BMABP), and Aortic Mean Arterial Blood Pressure (AMABP). Though not quite reaching the p<0.10 level designating a trend, clear differences between treatments were evident for Brachial Pulse Pressure (BPP) and Aortic Pulse Pressure (APP).

Post hoc power analyses were carried out to indicate whether the study was sufficiently powered to detect differential treatments at the p<0.05 level. Where said post hoc analysis indicated insufficient power, a priori power analyses were carried out to determine the sample size required to reach statistical power. The results of the power analysis showed that recruitment and inclusion of an additional six participants into the analysis (Total Analysis N=31) as planned following pandemic-related closures will make the analysis sufficiently powered to detect a significant interaction effect at the p<0.05 level for the above measures (BSBP, BMABP, AMABP, BPP and APP), if such effects exist.

Power analysis was performed using G*Power (version 3.1). The a error probability was set at 0.05, the number of groups was set at 2 (Treatment 1 & Treatment 2), and the number of measurements was set at four (pre-dose & post-dose, per treatment). The sample size for each analysis was 25 participants.

Example 5

Acute Effect of DHA Treatment on Cognitive Performance

Cognitive function was assessed using the Swinburne University Computerised Cognitive Ageing Battery (SUC-CAB). The battery is a computerized test battery of 8 tasks designed to capture the range of cognitive functions that decline with age, consisting of Simple Reaction Time, Choice Reaction Time, Immediate/Delayed Recognition, Stroop Colour-Word congruent/incongruent, Spatial Working Memory and Contextual Memory (Pipingas et al., (2010), *Curr Top Nutraceut Res* 8:79-87). All tasks were administered during pre-dose and post-dose testing on each testing day, with different versions of the battery used for each assessment.

The primary outcome measured was mean response time on each task. An additional cognitive outcome is the Stroop Effect. The Stroop Effect reflects inhibitory control (i.e. ability to ignore one stimulus in order to respond to another) and is calculated by subtracting mean Congruent Stroop response time from mean Incongruent Stroop response time. A smaller Stroop Effect (measured in milliseconds) reflects better inhibitory control. The SUCCAB tasks were as follows:

Simple Reaction Time (SRT): In this task a white square was displayed on the screen for 750 ms. Participants responded by pressing the 'yes' response button as quickly as possible each time the square was presented.

Complex Reaction Time (CRT): Participants were shown either a blue triangle or a red square displayed for 750 ms.

In this task participants responded each time the triangle or square was presented by pressing the corresponding coloured button on the button box.

Immediate Picture Recognition (IPR) (immediate recognition memory): During memory encoding, a series of 30 abstract images were be presented on the screen for 4 seconds each. Participants were instructed that their memory would be tested on these images immediately after they had viewed all of the images and again after approximately 20 minutes. During memory response, a second series of 30 images were shown, where 15 images were the same as the ones previously presented during encoding and 15 were new. A 'yes' button press indicated that the image had been recognized, whereas a 'no' button press indicated the image was new.

Stroop Congruent (CS): In this task, the words 'red', 'blue', 'green' or 'yellow' were presented on the screen in corresponding coloured ink. Participants were required to respond to the word by pressing the same coloured button.

Stroop Incongruent (ICS): Similar to the stroop congruent task the words 'red', 'blue', 'green' or 'yellow' were pre- Delayed Picture Recognition (DPR) (delayed recognition memory): This task was the follow-up to the immediate recognition memory task. A series of 30 images were shown, where half of the images were the same as the ones previously seen during the initial recognition memory task and the other half had not been previously presented. A 'yes' button press indicated that the image had been recognized, whereas a 'no' button press indicated the image was new.

Descriptive statistics for task response times by assessment time are given in Table 3 below. Response time change scores (milliseconds) were calculated for each treatment by subtracting the pre-dose response time from the post-dose response time for each cognitive task. The extent to which response time for each SUCCAB task changed from the pre-dose to post-dose for either treatment is displayed in FIG. 4.

TABLE 3

Descriptive Statistics for SUCCAB Task Response Times.

| SUCCAB Task | Treatment 1 Pre-dose | | Treatment 1 Post-dose | | Treatment 2 Pre-dose | | Treatment 2 Post-dose | |
|---|---|---|---|---|---|---|---|---|
| | Mean | SD | Mean | SD | Mean | SD | Mean | SD |
| Simple Reaction Time | 269.39 | 31.31 | 276.69 | 41.12 | 274.04 | 33.61 | 282.25 | 36.64 |
| Choice Reaction Time | 462.24 | 71.43 | 460.65 | 68.18 | 472.04 | 55.47 | 466.09 | 74.16 |
| Immediate Recognition Memory | 1067.08 | 292.15 | 953.03 | 164.99 | 1074.24 | 222.80 | 961.98 | 147.67 |
| Congruent Stroop | 723.07 | 77.18 | 666.49 | 70.79 | 710.19 | 77.18 | 667.57 | 75.84 |
| Incongruent Stroop | 852.89 | 111.43 | 810.26 | 95.67 | 866.60 | 142.63 | 802.70 | 137.33 |
| Stroop Effect | 129.82 | 87.56 | 143.76 | 82.87 | 156.41 | 105.54 | 135.14 | 97.24 |
| Spatial Working Memory | 911.56 | 240.09 | 898.14 | 209.51 | 983.96 | 306.59 | 914.25 | 212.62 |
| Contextual Memory | 1007.72 | 215.31 | 979.12 | 173.31 | 1052.85 | 261.66 | 1000.68 | 199.63 |
| Delayed Recognition Memory | 1087.22 | 185.64 | 1074.62 | 219.58 | 1057.80 | 151.11 | 1066.50 | 168.23 | sented on the screen, however, this time the word was different to the ink colour. Participants were required to ignore the written word and to respond to the colour of the ink by pressing the same coloured button.

Spatial Working Memory (SWM): In this task, a 4×4 grid was presented on the screen for 2950 ms, with 6 grid locations filled with a white square. The white squares then disappeared and the grid was empty for 1950 ms. A single white square was then shown in the grid for 1950 ms. A 'yes' response indicated that the white square was in the same position as one from the initial presentation, and a 'no' response indicated it was in a different location.

Contextual Recognition Memory (CRM): A series of 20 pictures of everyday objects were presented at a location either at the top, bottom, right or left of the screen for a total of 4 seconds each. A second series of the same images were then presented in centre of the screen. Participants responded by pressing the button which corresponded to the original location of the picture.

As demonstrated in FIG. 4, differential effects were observed in response time before and after treatment with DHA (treatment 2) compared to the placebo (treatment 1). In particular, stroop effect, ICS, SWM and CRM show marked reductions in response time.

Whilst the reductions in response time are not significant, following bias correction (i.e. data transformation to ameliorate a skewed data distribution), mean Stroop Effect response time (transformed) began trending towards a significant interaction effect ($p=0.086$) with seemingly better inhibitory control occurring after consumption of treatment 2. Post hoc power analysis revealed that inclusion of an additional six participants into the analysis (i.e. Total N=31) as planned will sufficiently power the analysis to detect a significant interaction at the $p<0.05$, if one exists, for Stroop Effect.

Similarly, Spatial Working Memory (SWM) and Contextual Recognition Memory (CRM) show what appear to be differential treatment effects. Although the apparent differential treatment effects are not significant for either SWM response time (p=0.32, bias corrected) nor CRM response time (p=0.469, bias corrected), power analyses, based on the current effect sizes, indicate the inclusion of an additional six participants in the analysis (Total Analysis N=31) as planned would power the SWM analysis to detect an interaction effect at the p<0.05 level, if one exists. A total sample of 52 would be required to sufficiently power the CRM analysis.

Incongruent Stroop (ICS) had no outliers (Z score>3.29) but was observed to have a positive skew. However, though there was a significant main effect of time upon ICS response time (transformed), there was no significant main effect of treatment, nor was there any evidence for a significant interaction effect. ICS post hoc power analysis indicates that in order to detect a significant interaction (p<0.05), an additional 11 participants are required (Total analysis N=36).

The invention claimed is:

1. A method for acutely reducing blood pressure or pulse pressure in a subject, the method comprising administering to the subject docosahexaenoic acid (DHA).

2. The method of claim 1, wherein the DHA is present in triglyceride form, ethyl ester form, phospholipid form, or free fatty acid form.

3. The method of claim 1, wherein the DHA is LCPUFAs are present in one or more DHA-containing oils.

4. The method of claim 3, wherein the one or more DHA-containing oils comprise an oil obtained from a single cell organism, a plant oil or a fish oil, or a concentrated form thereof.

5. The method of claim 1, wherein the DHA is administered in a dose of at least about 500 mg.

6. The method of claim 5, wherein the DHA is administered in a dose of about 4 g.

7. The method of claim 1, wherein the reduction in blood pressure or pulse pressure in the subject occurs within about 4 hours of administration of the DHA.

8. The method of claim 1, wherein the DHA is administered orally.

9. The method of claim 8, wherein the DHA is added to a food or drink for consumption by the subject prior to administration.

10. The method of claim 1, wherein the reduction in blood pressure comprises a reduction in brachial systolic blood pressure and/or in aortic systolic blood pressure, a reduction in brachial and/or aortic diastolic blood pressure, and/or a reduction in brachial and/or aortic mean arterial blood pressure.

11. The method of claim 1, wherein the reduction in pulse pressure comprises a reduction in brachial pulse pressure and/or a reduction in aortic pulse pressure.

* * * * *